United States Patent [19]

Lyons et al.

[11] 4,191,839
[45] Mar. 4, 1980

[54] DIRECT OXIDATION OF TOLUENE TO BENZYLIDENE DIACETATE

[75] Inventors: James E. Lyons, Wallingford; Robert W. Shinn, Aston; George Suld, Springfield, all of Pa.

[73] Assignee: Suntech, Inc., Philadelphia, Pa.

[21] Appl. No.: 890,175

[22] Filed: Mar. 27, 1978

[51] Int. Cl.[2] .................. C07C 67/05; C07C 69/16
[52] U.S. Cl. .................. 560/241; 260/599; 560/131; 568/815
[58] Field of Search ........................... 560/241

[56] References Cited

U.S. PATENT DOCUMENTS

| 3,442,954 | 5/1969 | Crocker | 560/241 |
| 3,547,982 | 12/1970 | McKeon et al. | 560/241 |
| 3,780,094 | 12/1973 | Herz | 560/241 |
| 4,156,783 | 5/1979 | Lyons et al. | 560/263 |

FOREIGN PATENT DOCUMENTS 1244080  8/1971  United Kingdom ..................... 560/131

OTHER PUBLICATIONS

Grozhan et al, Doklady Akad. Nauk SSSR, 204, No. 4, 872-873, Jun. 1972.

*Primary Examiner*—Vivian Garner
*Attorney, Agent, or Firm*—J. Edward Hess; Donald R. Johnson; Stanford M. Back

[57] ABSTRACT

A highly selective, one-step conversion of toluene to benzylidene diacetate is provided by the reaction of toluene with $O_2$ and acetic anhydride in the presence of an acid catalyst. No metal catalysts are required.

6 Claims, No Drawings

DIRECT OXIDATION OF TOLUENE TO BENZYLIDENE DIACETATE

BACKGROUND OF THE INVENTION

This invention relates to a process for the preparation of benzylidene diacetate. More particularly, this invention relates to a highly selective one-step conversion of toluene to benzylidene diacetate in the presence of acetic anhydride. Benzylidene diacetate is useful both as a high octane fuel component, and as a component in the preparation of heat stabilized polyoxymethylene (U.S. Pat. No. 3,293,220).

U.S. Pat. No. 3,547,982 discloses that during the conversion of toluene to benzyl acetate using acetic acid, metal acetate, and a complex palladium-based catalyst, small amounts of benzylidene diacetate are formed. Thus, this process is characterized by the formation of minor amounts of the diacetate, with selectivities of less than 20%. Other related prior art will be found in U.S. Pat. No. 3,772,383, British Pat No. 1,244,080 and French Pat. No. 1,397,083.

SUMMARY OF THE INVENTION

In accordance with the present invention it has now been found that toluene can be converted to benzylidene diacetate in a simple, one-step reaction by oxidizing toluene with air or oxygen in the presence of acetic anhydride and an acid catalyst such as benzene sulfonic acid, as shown by the reaction

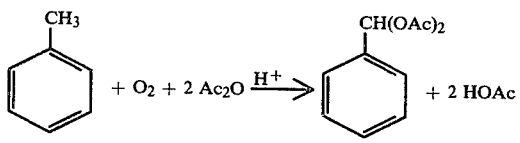

Suprisingly, this reaction is characterized by selectivities for benzylidene diacetate of up to 82%, while at the same time avoiding the need for costly metal complex catalysts.

DESCRIPTION OF THE INVENTION

The process of this invention is conveniently carried out under elevated temperatures of from about 75° to 200° C., preferably 100° to 150° C., and pressures of from about 1 to 50 atmospheres, in an autoclave for periods which are dependant upon the pressures and temperatures selected. The molar ratio of toluene to acetic anhydride is desirably from 2 to 8, and preferably 4 to 6. The range of concentration of acid catalyst employed is from about $10^{-2}$ to $10^{-5}$ moles/liter preferably $10^{-3}$ to $10^{-4}$ moles/liter.

Air may be used in place of $O_2$, in which case the amounts are increased proportionately to provide an equivalent amount of $O_2$.

The acid catalysts employed include alkyl or aryl sulfonic acids, phosphoric acid, or alkyl or aryl phosphonic acids. As stated above, the preferred acid catalyst is benzene sulfonic acid. Alternatively, however, there may be used such acids as toluene sulfonic acid, methane sulfonic acid, benzene phosphonic acid, and the like, as well as the aforestated phosphoric acid.

If desired, small amounts of initiators such as azobisisobutyronitrile, dibenzoylperoxide, and the like may be added to help initiate oxidation. Generally, about 0.2 wt.%, is sufficient for this purpose.

As shown by the examples below, there is obtained, in addition to the desired benzylidene diacetate, minor amounts of by-products including benzyl acetate, cresyl acetate, and phenoxymethyl acetate. The benzylidene diacetate may readily be recovered from the product mixture by distillation, followed by crystallization from ether.

The invention will now be illustrated by, but not limited to, the following examples, in which Examples 1-4 represent the novel process of this invention. Examples 5 and 6 are control examples illustrating that virtually no benzylidene diacetate is obtained when either the acid catalyst or the acetic anhydride is omitted, while Example 7 illustrates that not all strong organic acids will catalyze this reaction.

EXAMPLE 1

Toluene, 50 ml, acetic anhydride, 11.4 ml and benzene sulfonic acid, 0.20 grams, were reacted with air (145 psi) at 200° C. for 30 minutes. After this time period 3% of the toluene had been converted to products. Analysis of the reaction mixture was carried out by standardized glpc. Selectivities to products are given in parenthesis: benzylidene diacetate (60%), benzyl acetate (22%), cresyl acetates (7%), phenoxymethyl acetate (4%), others (9%).

EXAMPLE 2

Using the procedure of Example 1, but substituting phosphoric acid, 0.20 grams, for benzenesulfonic acid, 6% of the toluene was converted after 30 minutes. Product selectivities were: benzylidene diacetate (35%), benzyl acetate (43%), cresyl acetates (6%), phenoxymethyl acetate (2%), others (14%).

EXAMPLE 3

Toluene, 40 ml, acetic anhydride, 10 ml, dibenzoyl peroxide 0.3 gram and benzene sulfonic acid, 0.20 grams were reacted with oxygen (1 atm) at 105° C. for 30 hours. After this time, 3% of the toluene had been converted to products. Selectivity to benzylidene diacetate was 88%.

EXAMPLE 4

Using the procedure of Example 3, but substituting phosphoric acid for benzene sulfonic acid, 4% of the toluene was reacted in 30 hours. Selectively to benzylidene diacetate was 82%.

EXAMPLE 5

Using the procedure of Example 1 but using no acid catalyst, 4% of the toluene was converted after 30 minutes. Product selectivities were: benzylidene diacetate (2%), benzaldehyde (25%), benzyl acetate (67%), others (6%).

EXAMPLE 6

Using the procedure of Example 2, but using no acetic anhydride, only two major products were formed in similar amounts: benzaldehyde and benzyl alcohol.

EXAMPLE 7

Toluene, 40 ml, acetic anhydride, 10 ml. dibenzoyl peroxide, 0.3 gram and trifluoroacetic acid, 0.2 grams, were reacted with oxygen (1 atm) at 105° C. for 30 hours. After this time 2% of the toluene had been converted but no benzylidene diacetate was formed. Products were benzyl acetate and benzaldehyde in approximately equal amounts.

The invention claimed is:

1. A process for the production of benzylidene diacetate which comprises reacting toluene with air or oxygen at elevated temperatures of from about 75° to 200° C. and at pressures of from about 1 to 50 atmospheres in the presence of acetic anhydride and a strong acid catalyst consisting essentially of an alkyl or aryl sulfonic acid, an alkyl or aryl phosphonic acid, or phosphoric acid.

2. The process of claim 1 wherein the acid catalyst is benzene sulfonic acid.

3. The process of claim 1 wherein the temperature is in the range of about 100°–150° C.

4. The process of claim 1 wherein the mole ratio of toluene to acetic anhydride is 2 to 8.

5. The process of claim 1 wherein the acid catalyst is present in amounts of $10^{-2}$ to $10^{-5}$ moles/liter.

6. The process of claim 1 wherein an oxidation initiator is added.

* * * * *